(12) United States Patent
Edmondson, III et al.

(10) Patent No.: US 11,600,366 B2
(45) Date of Patent: Mar. 7, 2023

(54) SYSTEM AND METHOD FOR FACILITATING CONFIGURATION MODIFICATIONS FOR A PATIENT INTERFACE COMPUTER SYSTEM BASED ON RISK OF READMISSION OF A PATIENT

(71) Applicant: KONINKLIJKE PHILIPS N.V., Eindhoven (NL)

(72) Inventors: Thomas Lee Edmondson, III, Baltimore, MD (US); Karsten Anthony Alexander Russell-Wood, York, PA (US); Bridgette Leonard, Framingham, MA (US)

(73) Assignee: Koninklijke Philips N.V., Eindhoven (NL)

( * ) Notice: Subject to any disclaimer, the term of this patent is extended or adjusted under 35 U.S.C. 154(b) by 234 days.

(21) Appl. No.: 16/482,584

(22) PCT Filed: Jan. 24, 2018

(86) PCT No.: PCT/EP2018/051650
§ 371 (c)(1),
(2) Date: Jul. 31, 2019

(87) PCT Pub. No.: WO2018/141598
PCT Pub. Date: Aug. 9, 2018

(65) Prior Publication Data
US 2020/0013489 A1    Jan. 9, 2020

Related U.S. Application Data

(60) Provisional application No. 62/454,080, filed on Feb. 3, 2017.

(51) Int. Cl.
*G16H 10/60*     (2018.01)
*G16H 40/20*     (2018.01)
(Continued)

(52) U.S. Cl.
CPC .......... *G16H 10/60* (2018.01); *A61B 5/0022* (2013.01); *G16H 40/20* (2018.01); *G16H 50/20* (2018.01); *G16H 50/30* (2018.01)

(58) Field of Classification Search
CPC ........ G16H 10/60; G16H 40/20; G16H 50/30; G16H 50/20; G16H 40/63; G16H 40/67; A61B 5/0022
See application file for complete search history.

(56) References Cited

U.S. PATENT DOCUMENTS

| 2013/0346105 A1 | 12/2013 | Ryan et al. |
| 2014/0200915 A1 | 7/2014 | Ryan et al. |

(Continued)

FOREIGN PATENT DOCUMENTS

WO    WO-2012176104 A1 * 12/2012 ............. G16H 50/20

OTHER PUBLICATIONS

Li, Yue; Cai, Xueya; Yin, Jun; Glance, Laurent; Mukamel, Dana. "Is Higher Volue of Postacute Care Patients Associated With a Lower Rehospitalization Rate in Skilled Nursing Facilities?" Med Care Res Rev 2012 69: 103. Aug. 1, 2011 (Year: 2011).*

(Continued)

*Primary Examiner* — Linh Giang Le

(57) ABSTRACT

The present disclosure pertains to a system for facilitating configuration modifications for a patient interface computer system based on risk of readmission of the patient. In some embodiments, the system obtains (i) patient demographics information associated with a patient, the patient previously having been admitted at a facility of a first type, (ii) disease information associated with the patient, and (iii) facility information associated with a facility of a second type, the facility information including one or more facility-specific factors associated with the facility of the second type. The system determines a risk of readmission to a facility of the (Continued)

first type for the patient based on the obtained patient demographics information, the disease information, and the facility information. The system causes a configuration of the patient interface computer system to be modified based on the determined risk of readmission.

10 Claims, 3 Drawing Sheets

(51) Int. Cl.
    *G16H 50/30*     (2018.01)
    *G16H 50/20*     (2018.01)
    *A61B 5/00*     (2006.01)

(56) References Cited

U.S. PATENT DOCUMENTS

2014/0350967 A1    11/2014    Geleijnse et al.
2015/0261924 A1    9/2015    Geleijnse et al.
2015/0339791 A1*    11/2015    Tetteh ............... G16H 50/20
    705/2
2015/0363568 A1    12/2015    Milo et al.
2016/0188834 A1    6/2016    Erdmann et al.

OTHER PUBLICATIONS

Singh, Siddhartha; Lin, Yu-Li; Kuo, Yong-Fang; Nattinger, Ann B.; Goodwin, James S. "Variation in the Risk of Readmission Among Hospitals: The Relative Contribution of Patient, Hospital and Inpatient Provider Characteristics." Journal of General Internal Medicine. 29.4: 572-578. (Apr. 2014) (Year: 2014).*
Van Walraven C, Dhalla IA, Bell C, et al. Derivation and validation of an index to predict early death or unplanned readmission after discharge from hospital to the community. CMAJ. 2010;182(6):551-557].
Donzé JD, Williams MV, Robinson EJ, et al. International Validity of the HOSPITAL Score to Predict 30-Day Potentially Avoidable Hospital Readmissions. JAMA Intern Med 2016; 176:496.
International Search Report and Written Opinion, International Application No. PCT/EP2018/051650, dated Apr. 18, 2018.

* cited by examiner

SYSTEM AND METHOD FOR FACILITATING CONFIGURATION MODIFICATIONS FOR A PATIENT INTERFACE COMPUTER SYSTEM BASED ON RISK OF READMISSION OF A PATIENT

CROSS-REFERENCE TO PRIOR APPLICATIONS

This application is the U.S. National Phase application under 35 U.S.C. § 371 of International Application No. PCT/EP2018/051650, filed on 24 Jan. 2018, which claims the benefit of U.S. Provisional Patent Application No. 62/454,080, filed on 3 Feb. 2017. These applications are hereby incorporated by reference herein.

BACKGROUND

1. Field

The present disclosure pertains to a system and method for determining risk of readmission to a facility of a first type for a patient to be admitted to a facility of a second type and/or facilitating configuration modifications for a patient interface computer system based on the determined risk of readmission.

2. Description of the Related Art

Following a hospital stay, individuals often rely on rehabilitation facilities (e.g., skilled nursing facilities) to recover. Although computer-assisted readmission risk determination systems exist, such risk determination systems fail to consider environmental factors specific to a rehabilitation facility and/or other factors in determining a patient's risk of readmission from the rehabilitation facility to a hospital. Thus, such risk determination systems may fail to identify patients who are at an increased risk due to non-traditionally considered factors (e.g., multi-morbid conditions, disability, environmental factors affecting the care process, etc.), but who may nevertheless be at risk due to facility-specific or other environmental factors.

SUMMARY

Accordingly, one or more aspects of the present disclosure relate to a system configured to facilitate configuration modifications for a patient interface computer system based on risk of readmission of a patient. The system comprises one or more processors and/or other components. The one or more processors are configured by machine-readable instructions to: obtain patient demographics information associated with a patient, the patient previously having been admitted at a facility of a first type; obtain disease information associated with the patient; obtain facility information associated with a facility of a second type to which the patient has been admitted subsequent to the facility of the first type, the facility information including one or more facility-specific factors associated with the facility of the second type; determine a risk of readmission to a facility of the first type for the patient based on the obtained patient demographics information, the disease information, and the facility information; and cause a configuration of the patient interface computer system to be modified based on the determined risk of readmission.

Yet another aspect of the present disclosure relates to a method for facilitating configuration modifications for a patient interface computer system based on risk of readmission of a patient with a system. The system comprises one or more processors and/or other components. The method comprises: obtaining, with the one or more processors, patient demographics information associated with a patient, the patient previously having been admitted at a facility of a first type; obtaining, with the one or more processors, disease information associated with the patient; obtaining, with the one or more processors, facility information associated with a facility of a second type to which the patient has been admitted subsequent to the facility of the first type, the facility information including one or more facility-specific factors associated with the facility of the second type; determining, with the one or more processors, a risk of readmission to a facility of the first type for the patient based on the obtained patient demographics information, the disease information, and the facility information; and causing, with the one or more processors, a configuration of the patient interface computer system to be modified based on the determined risk of readmission.

Still another aspect of present disclosure relates to a system for facilitating configuration modifications for a patient interface computing system based on risk of readmission of a patient. The system comprises: means for obtaining patient demographics information associated with a patient, the patient previously being admitted at a facility of a first type; means for obtaining disease information associated with the patient; means for obtaining facility information associated with a facility of a second type to which the patient has been admitted subsequent to the facility of the first type, the facility information including one or more facility-specific factors associated with the facility of the second type; means for determining a risk of readmission to a facility of the first type for the patient based on the obtained patient demographics information, the disease information, and the facility information; and means for causing a configuration of the patient interface computer system to be modified based on the determined risk of readmission.

These and other objects, features, and characteristics of the present disclosure, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the disclosure.

DETAILED DESCRIPTION OF EXEMPLARY EMBODIMENTS

Figure 1:
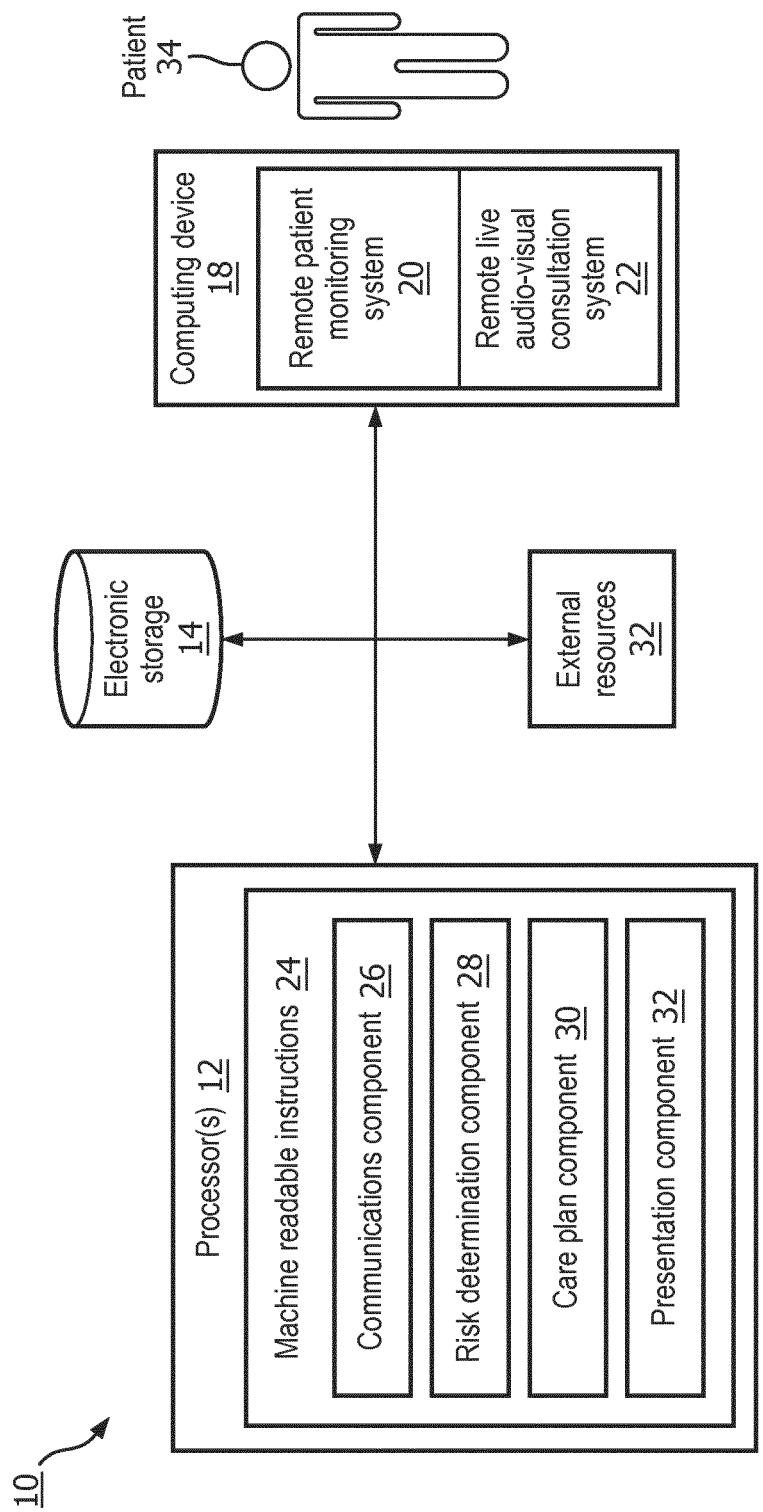
FIG. 1 is a schematic illustration of a system for facilitating configuration modifications for a patient based on risk of readmission of the patient, in accordance with one or more embodiments.

As used herein, the singular form of "a", "an", and "the" include plural references unless the context clearly dictates otherwise. As used herein, the term "or" means "and/or" unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

FIG. 1 is a schematic illustration of a system 10 for facilitating configuration modifications for a patient based on risk of readmission of the patient. In some embodiments, a facility of a first type may include a hospital, an urgent care facility, an acute care facility, a primary care facility, an emergency department, and/or other facilities. In some embodiments, a facility of a second type may include a skilled nursing facility, an assisted living facility, an independent living facility, a continuing care retirement community, a residential care home, a personal care home, and/or other facilities. In the setting of a second-type facility, a value of screening tools to identify newly admitted patients to the second-type facility at risk of return to a first-type facility is likely affected by both clinical issues and system level issues, which vary by region and facility. System 10 stratifies patients according to their risk of return to the first-type facility and identifies modifiable risk factors that may be addressed in order to prevent a return to the first-type facility. System 10 stratifies the patients upon admission to a second-type facility from a first-type facility or when a patient residing in a second-type facility experiences a change of condition. Responsive to a determination of an elevated risk of readmission due to one or more second-type facility-specific factors, system 10 causes a configuration of a patient interface computer system to be modified based on the determined risk of readmission. For example, system 10 may schedule one or more remote consultation sessions with one or more care givers (e.g., clinicians, doctors, nurses, dieticians, physical therapists, central care coordinators, etc.) for the patient via a remote live audio-video consultation system. As another example, system 10 may change a monitoring frequency of one or more sensors associated with the patient based on the determined risk of readmission. In yet another example, system 10 may add or remove user interface options associated with a wearable device and/or other computing devices responsive to an increased and/or decreased risk of readmission.

System 10 is configured to reduce the likelihood of a return to a first type facility by determining a risk of readmission based on physiological observations, measurements, survey responses, facility-specific factors, and/or other information and causing a configuration of a patient interface computer system to be modified based on the determined risk of readmission. In some embodiments, system 10 comprises one or more processors 12, electronic storage 14, external resources 16, computing device 18, and/or other components.

In some embodiments, computing device 18 includes a remote patient monitoring system 20 and a remote live audio-visual consultation system 22. Remote patient monitoring system may include one or more sensors configured to generate output signals conveying information related to physiological characteristics and/or disease information associated with patient 34. In some embodiments, the one or more sensors include but are not limited to equipment used in hospitals, doctor's offices, and/or other medical facilities, in the home of patient 34, and/or in other locations to monitor vital signs and/or other physiological information (e.g., pulse rate monitors, blood pressure monitors, blood oxygenation monitors, glucose monitors, weight scales, thermometers, electrocardiogram (EKG) equipment, childbirth labor contraction monitors, etc.), test equipment (e.g., imaging equipment such as an MRI and/or an x-ray machine, an ultrasound, electroencephalogram (EEG) equipment, etc.), equipment for treating patient 34 (e.g., respirators/ventilators, light therapy devices, etc.), and/or other devices. In some embodiments, information from the one or more sensors may be automatically transmitted to computing device 18, one or more remote servers, or other destinations via one or more networks (e.g., local area networks, wide area networks, the Internet, etc.).

Figure 2:
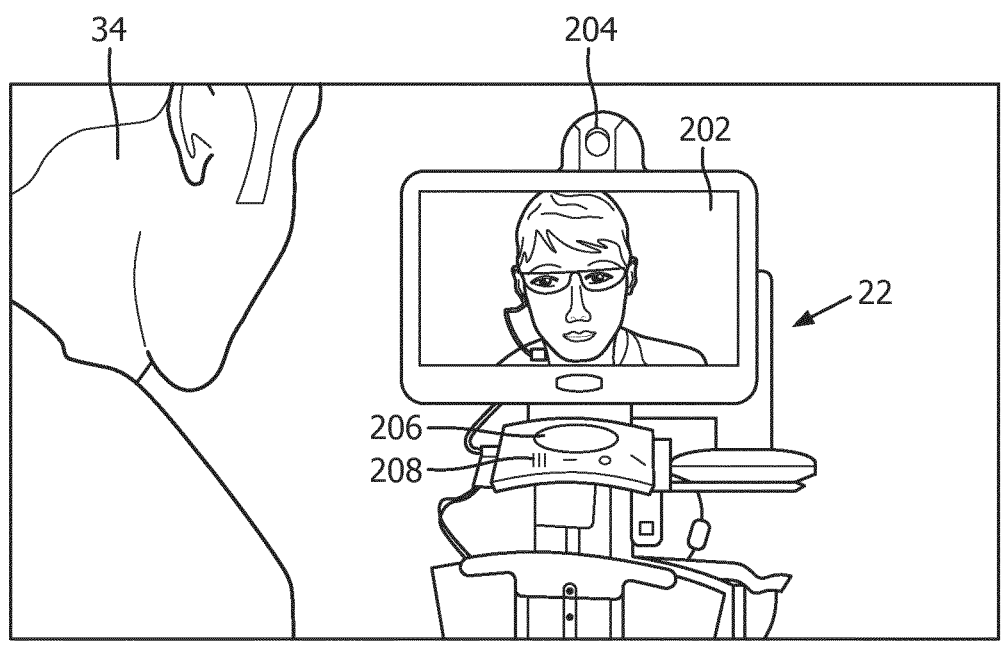
FIG. 2 illustrates a remote live audio-visual consultation system, in accordance with one or more embodiments.

In some embodiments, remote live audio-visual consultation system 22 includes one or more interface devices (described below) capable of transmitting and receiving audio/video and data. By way of a non-limiting example, FIG. 2 illustrates a remote live audio-visual consultation system, in accordance with one or more embodiments. As shown in FIG. 2, remote live audio-visual consultation system 22 includes one or more of a display 202, a camera 204, a speaker 206, a microphone 208, and/or other interface devices to enable the one or more care givers to evaluate patient 34, foster care plan compliance, provide immediate access to patient feedback, and/or enhance self-care abilities of patient 34.

Computing device 18 is configured to provide an interface between patient 34, caregivers, and system 10. In some embodiments, computing device 18 is associated with individual caregivers, a central caregiver coordinator, and/or other users. Computing device 18 is configured to provide information to and/or receive information from patient 34, caregivers, and/or other users. Computing device 18 includes a user interface and/or other components. The user interface may be and/or include a graphical user interface configured to present caregivers with views and/or fields configured to receive entry and/or selection of information related to patient 34 and/or provide and/or receive other information. In some embodiments, the user interface includes a plurality of separate interfaces associated with a plurality of computing devices 18, processor 12, and/or other components of system 10, for example.

In some embodiments, computing device 18 is configured to provide the user interface, processing capabilities, databases, and/or electronic storage to system 10. As such, computing device 18 may include processor 12, electronic storage 14, external resources 16, and/or other components of system 10. In some embodiments, computing device 18 is connected to a network (e.g., the internet). In some embodiments, computing device 18 does not include processor 12, electronic storage 14, external resources 16, and/or other components of system 10, but instead communicate with these components via the network. The connection to the network may be wireless or wired. For example, processor 12 may be located in a remote server and may wirelessly cause display of the risk of readmission via the user interface to a caregiver on a computing device 18 associated with that caregiver (e.g., a doctor, a nurse, a central caregiver coordinator, etc.). In some embodiments, computing devices 18 are laptops, desktop computers, smartphones, tablet computers, and/or other computing devices.

Examples of interface devices suitable for inclusion in the user interface include a camera, a touch screen, a keypad, touch sensitive and/or physical buttons, switches, a keyboard, knobs, levers, a display, speakers, a microphone, an indicator light, an audible alarm, a printer, and/or other interface devices. The present disclosure also contemplates that computing device 18 includes a removable storage interface. In this example, information may be loaded into computing device 18 from removable storage (e.g., a smart card, a flash drive, a removable disk) that enables caregivers and/or other users to customize the implementation of computing device 18. Other exemplary input devices and techniques adapted for use with computing device 18 and/or the user interface include, but are not limited to, an RS-232 port, RF link, an IR link, a modem (telephone, cable, etc.) and/or other devices.

Processor 12 is configured to provide information processing capabilities in system 10. As such, processor 12 may comprise one or more of a digital processor, an analog processor, a digital circuit designed to process information, an analog circuit designed to process information, a state machine, and/or other mechanisms for electronically processing information. Although processor 12 is shown in FIG. 1 as a single entity, this is for illustrative purposes only. In some embodiments, processor 12 may comprise a plurality of processing units. These processing units may be physically located within the same device (e.g., a server), or processor 12 may represent processing functionality of a plurality of devices operating in coordination (e.g., one or more servers, computing device 18, devices that are part of external resources 16, electronic storage 14, and/or other devices.)

In some embodiments, processor 12, electronic storage 14, external resources 16, computing device 18, and/or other components may be operatively linked via one or more electronic communication links. For example, such electronic communication links may be established, at least in part, via a network such as the Internet, and/or other networks. It will be appreciated that this is not intended to be limiting, and that the scope of this disclosure includes embodiments in which these components may be operatively linked via some other communication media. In some embodiments, processor 12 is configured to communicate with electronic storage 14, external resources 16, computing device 18, and/or other components according to a client/server architecture, a peer-to-peer architecture, and/or other architectures.

As shown in FIG. 1, processor 12 is configured via machine-readable instructions 24 to execute one or more computer program components. The one or more computer program components may comprise one or more of a communications component 26, a risk determination component 28, a care plan component 30, a presentation component 32, and/or other components. Processor 12 may be configured to execute components 26, 28, 30, and/or 32 by software; hardware; firmware; some combination of software, hardware, and/or firmware; and/or other mechanisms for configuring processing capabilities on processor 12.

It should be appreciated that although components 26, 28, 30, and 32 are illustrated in FIG. 1 as being co-located within a single processing unit, in embodiments in which processor 12 comprises multiple processing units, one or more of components 26, 28, 30, and/or 32 may be located remotely from the other components. The description of the functionality provided by the different components 26, 28, 30, and/or 32 described below is for illustrative purposes, and is not intended to be limiting, as any of components 26, 28, 30, and/or 32 may provide more or less functionality than is described. For example, one or more of components 26, 28, 30, and/or 32 may be eliminated, and some or all of its functionality may be provided by other components 26, 28, 30, and/or 32. As another example, processor 12 may be configured to execute one or more additional components that may perform some or all of the functionality attributed below to one of components 26, 28, 30, and/or 32.

Communications component 26 is configured to obtain patient demographics information associated with patient 34. In some embodiments, patient 34 has been previously admitted at a facility of a first type. In some embodiments, patient demographics information includes one or more of an age, years of education, whether or not patient 34 lives alone, marital status, number of children, code status (e.g., yes/no to CPR; yes/no to ET intubation; yes/no to hospitalization), and/or other information. In some embodiments, patient demographics information includes manually recorded information, results of an electronic survey, information in medical care provider databases (e.g., Medicare databases), and/or other information. In some embodiments, communications component 26 is configured to facilitate direct entry and/or selection of patient demographics information by patient 34 via computing device 18. In some embodiments, communications component 26 obtains patient demographics information stored in electronic storage 14, information stored in electronic medical record systems and/or other medical information systems of care providers associated with system 10 (e.g., servers and/or other databases that are part of external resources 16 such as Medicare databases, etc.), and/or information from other sources.

In some embodiments, communications component 26 is configured to obtain disease information associated with patient 34. In some embodiments, disease information includes one or more of hospital length of stay (including observation status days), number of emergency department visits within last 12 months, number of unplanned hospital admissions within last 12 months, serum sodium, serum hemoglobin, serum white blood cell count, and/or other information. In some embodiments, the disease information includes manually recorded information, test results, output from remote patient monitoring system 20 and/or other medical devices, information in medical care provider databases (e.g., Medicare databases) and/or other information. In some embodiments, communications component 26 obtains disease information associated with patient 34 stored in electronic storage 14, information stored in electronic medical record systems and/or other medical information systems of care providers associated with system 10 (e.g., servers and/or other databases that are part of external resources 16 such as Medicare databases, etc.), and/or information from other sources.

In some embodiments, communications component 26 is configured to obtain facility information associated with a facility of a second type to which patient 34 has been admitted subsequent to the first-type facility. The facility information may include one or more facility-specific factors associated with the facility of the second type. In some embodiments, the one or more facility-specific factors include one or more of the Centers for Medicare and Medicaid services rating, The Joint Commission certification status, a Resident Council meeting frequency, a Family Council meeting frequency, a number of deficiencies on a previous licensing and certification survey, visitation hour enforcement, a treating registered nurse to patient ratio, a licensed practical nurse and/or licensed vocational nurse to patient ratio, a geriatric nursing assistant and/or certified nursing assistant to patient ratio, information related to nurse use at the facility of the second type, a staff turnover rate, a root cause analysis percentage of unplanned admission and/or transfer to an emergency department, a return-to-hospital rate, information related to a medical director of the facility of the second type, and/or other information.

In some embodiments, communications component 26 is configured to obtain discharge date information from the facility of the first type associated with the patient. In some embodiments, discharge date information includes a number of days since discharge from a first-type facility, and/or other information. In some embodiments, discharge date information includes manually recorded information, information stored on databases associated with the second-type facility and/or a first-type facility (e.g., electronic medical record), and/or other information.

Risk determination component 28 is configured to determine a risk of readmission to a facility of the first type for the patient based on the obtained patient demographics information, the disease information, the facility information and/or the discharge date information. In some embodiments, risk determination component 28 is configured to assign a score to individual demographic-specific factors of the obtained patient demographics information, individual disease-specific factors of the disease information, individual facility-specific factors of the facility information, and/or individual factors of the discharge date information. For example, the score may include a scale ranging from −5 indicating reduced and/or the lowest risk to 10 indicating an increase and/or the highest risk. In some embodiments, scores assigned to individual ones of the obtained patient demographics information, the disease information, the facility information and the discharge date information may be weighted proportionally. By way of a non-limiting example, table 1 illustrates scores assigned to individual categories associated with the obtained patient demographics information, the disease information, the facility information and the discharge date information. In this example, the second-type facility includes a skilled nursing facility (SNF). As illustrated in table 1, the lowest potential total points for a risk of readmission may be −38 and the highest potential total points for a risk of readmission may be 194.

TABLE 1

| | | Assigned Score | Potential Total Points Per Risk Factor Category | |
|---|---|---|---|---|
| | | | Highest | Lowest |
| Patient Demographics | | | | |
| Age, years | 25-54 | 2 | | |
| | 55-74 | 0 | | |
| | 75-84 | 3 | | |
| | >85 | 5 | 5 | 0 |

TABLE 1-continued

| | | Assigned Score | Potential Total Points Per Risk Factor Category | |
|---|---|---|---|---|
| | | | Highest | Lowest |
| Years of Education | <8 | 5 | | |
| | 9-11 | 3 | | |
| | 12-16 | 0 | | |
| | >17 | 3 | 5 | 0 |
| Language (primary) | English | 0 | | |
| | Non-English primary | 5 | 5 | 0 |
| Marital Status | Single (Not married, widowed, divorced) | 5 | | |
| | Married or co-habitating | 0 | 5 | 0 |
| Caregiver available at home upon discharge from SNF | Yes | 0 | | |
| | No | 2 | 2 | 0 |
| Number of children | None | 7 | | |
| | 1-2 | 3 | | |
| | >3 | 0 | 7 | 0 |
| Code status | Yes to CPR | 4 | | |
| | No to CPR | 0 | | |
| | Yes to ET intubation | 4 | | |
| | No to ET intubation | 0 | | |
| | Yes to Hospitalization | 10 | | |
| | No to Hospitalization | −5 | 10 | −5 |
| Disease Information | | | | |
| Hospital LOS (includes observation status days) | 0-2 days | 3 | | |
| | 3-4 days | 0 | | |
| | 5-7 days | 5 | | |
| | >8 days | 7 | 7 | 0 |
| Number of ED visits in the last 12 months | 0-1 | 0 | | |
| | 2-3 | 5 | | |
| | >4 | 10 | 10 | 0 |
| Number of unplanned hospital admissions in last 12 months | 0 | 0 | | |
| | 1-2 | 3 | | |
| | >3 | 7 | 7 | 0 |
| Serum sodium | ≥146 | 3 | | |
| | 135-145 | 0 | | |
| | ≤134 | 3 | 3 | 0 |
| Serum hemoglobin | >12 | 0 | | |
| | 10-11.9 | 2 | | |
| | 7.0-9.9 | 4 | | |
| | <6.9 | 6 | 6 | 0 |
| Serum WBC, total | <3.5 | 1 | | |
| | 3.6-10.9 | 0 | | |
| | >11.0-13.0 | 1 | | |
| | >13.1-19.9 | 3 | | |
| | >20 | 5 | 5 | 0 |
| SNF-specific factors | | | | |
| Staff turnover, % | <30% | −2 | | |
| | 31-50% | 0 | | |
| | 51-70% | 5 | | |
| | ≥71% | 10 | 10 | −2 |
| Bedside, treating RN to patient ratio (as calculated on the previous business day) | 1 nurse: <6 patients | −5 | | |
| | 1 nurse: 7-9 patients | −2 | | |
| | 1 nurse: 10-13 patients Or RNs do not provide bedside care | 0 | | |
| | 1 nurse: >14 | 4 | 4 | −5 |

TABLE 1-continued

| | | Assigned Score | Potential Total Points Per Risk Factor Category | |
|---|---|---|---|---|
| | | | Highest | Lowest |
| Bedside, treating LPN/LVN to patient ratio (as calculated on the previous business day) | patients 1 nurse: <6 patients 1 nurse: 7-9 patients Or LPNs do not provide bedside care 1 nurse: 10-13 patients 1 nurse: 14-17 patients 1 nurse: >18 patients | -5 0 5 7 10 | 10 | -5 |
| GNA/CNA to patient ratio (as calculated on the previous business day) | 1 GNA: ≤5 patients 1 GNA: 6-8 patients 1 GNA: 9-11 patients 1 GNA: ≥12 patients | -5 0 5 10 | 10 | -5 |
| Agency nurse use (Number of shifts per week requiring coverage) | None ≤5 6-10 11-15 ≥16 | -3 0 5 7 10 | 10 | -3 |
| Medical Director | | | | |
| Certified as a CMD by ABPLM | Yes Not Certified | 0 7 | 7 | 0 |
| Number of hours in the building per week as Medical Director (not working as an attending physician) | 0-2 hrs 3 hrs to 5 hrs 6 hrs to 7 hrs >8 hrs | 8 6 0 -2 | 8 | -2 |
| CMS 5 star rating | 1-2 stars 3-4 stars 5 stars | 8 4 0 | 8 | 0 |
| The Joint Commission certified | Yes: lower risk No: no change in risk score | -1 0 | 0 | -1 |
| Resident Council | Meets monthly Meets bi-monthly Meets quarterly | 0 1 3 | 3 | 0 |
| Family Council | None Meets monthly Meets bi-monthly Meets quarterly | 8 0 2 4 | 8 | 0 |
| INTERACT | Present, optimally used Present but not used optimally Not present | 0 3 6 | 6 | 0 |
| Root Cause Analysis of each unplanned admission or transfer to the ED is performed | 90-100% reviewed 75-90% reviewed 50-74% reviewed <50% reviewed | -5 -2 3 6 | 6 | -5 |
| Return-to-hospital rate, baseline (QM) | 0-8% 9%-12% 13%-16% 17%-22% ≥23% | -4 -2 0 4 8 | 8 | -4 |
| Visiting Hours | Publicized but actively not enforced Enforced Visitors allowed 24/7 | 2 4 0 | 4 | 0 |
| Number of deficiencies on last licensing & certification survey | None 1 to 3 4 to 6 7 to 9 10 to 12 13 to 15 >15 | -2 0 2 4 6 8 10 | 10 | -2 |
| Date of Discharge from an Acute Care Hospital | | | | |
| Number of days since discharge | 0-7 8-14 15-21 22-30 >30 | 5 4 3 2 1 | 5 | 1 |
| Total Score | | | 194 | -38 |

In some embodiments, risk determination component 28 is configured to determine the risk of readmission based on a sum of the assigned scores. In some embodiments, risk determination component 28 is configured to stratify patient 34 into one or more risk levels based on the determined risk of readmission. For example, a level 1 risk indicating the lowest risk may include a total score ranging from −38 to 20; a level 2 risk indicating a low risk may include a total score ranging from 21 to 79; a level 3 risk indicating a medium risk may include a total score ranging from 80 to 138; and a level 4 risk indicating a high risk may include a total score ranging from 139 to 194.

Care plan component 30 is configured to cause a configuration of a patient interface computer system to be modified based on the determined risk of readmission. In some embodiments, the patient interface computer system may include one or more components of computing device 18, one or more wearable devices, and/or other computer systems. In some embodiments, configurations of the patient interface computer system to be modified may include one or more settings corresponding to remote patient monitoring system 20 (e.g., frequency of monitoring with one or more sensors, duration of monitoring with the one or more sensors, a particular time of day designated for monitoring one or more vital signs, physiological parameters, and/or other information), frequency, time, and/or duration of care giver consultations with patient 34, type of care giver to provide the consultation with patient 34 (e.g., nurse, specialist, and/or other care givers), and/or other configurations. For example, the patient interface computer system may include remote live audio-visual consultation system 22. In this example, care plan component 30 may schedule one or more remote consultation sessions with one or more care givers for patient 34 via remote live audio-video consultation system 22. By way of a non-limiting example, a display, a camera, a speaker, and a microphone may be used during a remote consultation session. Scheduling a remote consultation may include determining (i) a frequency of consultation (e.g., daily, weekly, and/or other frequencies), (ii) a time and/or duration of the consultation, (iii) a particular care giver and/or care giver type, and/or other information. As another example, the patient interface computer system may include remote patient monitoring system 20. In this example, care plan component 30 may change an amount of monitoring of patient 34 with remote patient monitoring system 20. In some embodiments, remote patient monitoring may occur at a particular time of the day, repeatedly occur every hour, 4 hours, 8 hours, 12 hours, and/or other periods and frequencies. Responsive to an elevated risk of readmission, care plan component 30 may, for example, change monitoring frequency of remote patient monitoring system 20 from once daily to every hour. In some embodiments, responsive to a decreased risk of readmission, care plan component 30 may lower a monitoring frequency of remote patient monitoring system 20 from hourly to every eight hours.

In yet another example, the patient interface computer system may include a wearable device (e.g., a smart watch or other wearable device). Configurations of the wearable system to be modified may include notifications, one or more types of notifications (e.g., alarms, reminders, directions), a frequency of notifications (e.g., hourly, six times, four times, or twice daily), displaying or hiding one or more options from a user interface associated with the wearable device, and/or other configurations. In some embodiments, care plan component 30 may be configured to, responsive to the determined risk of readmission, cause the wearable device to provide (i) a notification to patient 34 regarding a change in diet, (ii) a reminder regarding taking a particular medication, (iii) directions to an appropriate location within the second-type facility, and/other instructions. In some embodiments, responsive to an elevated risk of readmission, care plan component 30 may increase a number of user interface options associated with the wearable device. For example, user interface options corresponding to requesting a remote consultation, a request for emergency care, directions to the closest emergency department, and/or other options may be displayed. In some embodiments, responsive to a decreased risk of readmission, care plan component 30 may reduce, limit, and/or hide one or more user interface options associated with the wearable device.

In some embodiments, care plan component 30 is configured to modify a care plan associated with patient 34 based on the determined risk level. For example, care plan component 30 may be configured to, responsive to the determined risk level being low risk, provide a consultation on demand to patient 34. For example, care plan component 30 may cause a user interface associated with a wearable device associated with the patient to display an option for requesting a remote consultation with a care giver. As another example, care plan component 30 may be configured to, responsive to the determined risk level being medium risk, provide (i) a spot-check to patient 34 via remote patient monitoring system 20 and (ii) provide a consultation on demand to patient 34. Providing a spot-check to patient 34 may include obtaining, with remote patient monitoring system 20, one or more vital signs, physiological parameters, and/or other information associated with patient 34 irrespective of a duty cycle of remote patient monitoring system 20's monitoring frequency. By way of a non-limiting example, vital signs, physiological parameters, and/or other information associated with patient 34 may be obtained from one or more of a pulse rate sensor, a blood pressure sensor, a blood oxygenation sensor, and/or other sensors during a spot-check. In yet another example, care plan component 30 may be configured to, responsive to the determined risk level being high risk, continuously monitor patient 34 via remote patient monitoring system 20 and (ii) provide a consultation on demand to patient 34. Continuous monitoring of patient 34 may include long-term and/or periodic bedside monitoring of patient 34's vital signs, physiological parameters, and/or other information using remote patient monitoring system 20.

Presentation component 32 is configured to effectuate presentation of the determined risk of readmission to one or more care givers. In some embodiments, presentation component 32 is configured to notify the one or care givers regarding a change in the determined risk of readmission for patient 34. For example, presentation component 32 may display an alert on a computing device (e.g., wearable device, laptop, desktop) user interface associated with the one or more care givers indicating an increase in the risk of readmission for patient 34. As another example, presentation component 32 may, responsive to an elevated risk of readmission, display (i) an alert, (ii) one or more vital signs, physiological parameters, and/or other information associated with patient 34, (iii) a user interface option to remotely interact and/or consult with patient 34, and/or other information.

Electronic storage 14 comprises electronic storage media that electronically stores information. The electronic storage media of electronic storage 14 may comprise one or both of system storage that is provided integrally (i.e., substantially non-removable) with system 10 and/or removable storage that is removably connectable to system 10 via, for example, a port (e.g., a USB port, a firewire port, etc.) or a drive (e.g., a disk drive, etc.). Electronic storage 14 may be (in whole or in part) a separate component within system 10, or electronic storage 14 may be provided (in whole or in part) integrally with one or more other components of system 10 (e.g., a computing device 18, processor 12, etc.). In some embodiments, electronic storage 14 may be located in a server together with processor 12, in a server that is part of external resources 16, in computing device 18 associated with caregivers, and/or in other locations. Electronic storage 14 may comprise one or more of optically readable storage media (e.g., optical disks, etc.), magnetically readable storage media (e.g., magnetic tape, magnetic hard drive, floppy drive, etc.), electrical charge-based storage media (e.g., EPROM, RAM, etc.), solid-state storage media (e.g., flash drive, etc.), and/or other electronically readable storage media. Electronic storage 14 may store software algorithms, information determined by processor 12, information received via computing device 18 and/or other external computing systems, information received from external resources 16, and/or other information that enables system 10 to function as described herein. By way of a non-limiting example, electronic storage 14 may store the total score for the risk of readmission associated with patient 34 determined by risk determination component 28 of processor 12.

External resources 16 include sources of information (e.g., databases, websites, etc.), external entities participating with system 10 (e.g., a medical records system of a health care provider that stores patient demographics information, patient disease information, facility information, and discharge date information), external home monitoring systems, one or more servers outside of system 10, a network (e.g., the internet), electronic storage, equipment related to Wi-Fi technology, equipment related to Bluetooth® technology, data entry devices, sensors, scanners, and/or other resources. In some implementations, some or all of the functionality attributed herein to external resources 16 may be provided by resources included in system 10. External resources 16 may be configured to communicate with processor 12, computing device 18, electronic storage 14, and/or other components of system 10 via wired and/or wireless connections, via a network (e.g., a local area network and/or the internet), via cellular technology, via Wi-Fi technology, and/or via other resources. In some embodiments, external resources 16 includes a telehealth software platform (e.g., Philips eCare Coordinator) that enables one or more care givers to remotely monitor patient 34's vital signs and send one or more surveys to patient 34 about his/her health status. In some embodiments, the telehealth software platform may create new care plans based on patient-specific needs including risk of readmission, condition, language, cognition, and/or other factors.

Figure 3:
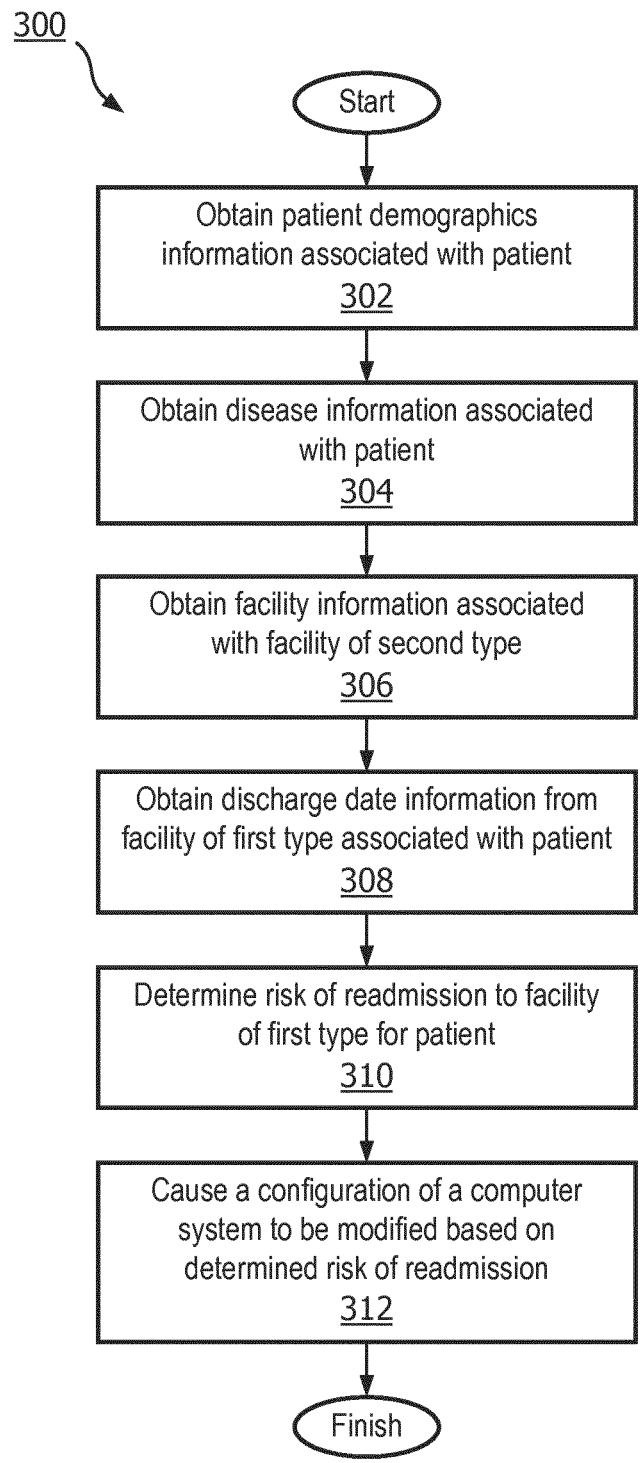
FIG. 3 illustrates a method for facilitating configuration modifications for a patient based on risk of readmission of the patient, in accordance with one or more embodiments.

FIG. 3 illustrates a method 300 for facilitating configuration modifications for a patient based on risk of readmission of the patient. Method 300 may be performed with a system. The system comprises one or more processors, and/or other components. The one or more processors are configured by machine readable instructions to execute computer program components. The computer program components include a communications component, a risk determination component, a care plan component, a presentation component, and/or other components. The operations of method 300 presented below are intended to be illustrative. In some embodiments, method 300 may be accomplished with one or more additional operations not described, and/or without one or more of the operations discussed. Additionally, the order in which the operations of method 300 are illustrated in FIG. 3 and described below is not intended to be limiting.

In some embodiments, method 300 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 300 in response to instructions stored electronically on an electronic storage medium. The one or more processing devices may include one or more devices configured through hardware, firmware, and/or software to be specifically designed for execution of one or more of the operations of method 300.

At an operation 302, patient demographics information associated with a patient is obtained. In some embodiments, the patient may have been previously admitted at a facility of a first type. In some embodiments, operation 302 is performed by a processor component the same as or similar to communications component 26 (shown in FIG. 1 and described herein).

At an operation 304, disease information associated with the patient is obtained. In some embodiments, operation 304 is performed by a processor component the same as or similar to communications component 26 (shown in FIG. 1 and described herein).

At an operation 306, facility information associated with a facility of a second type is obtained. In some embodiments, the facility information includes one or more facility-specific factors associated with the facility of the second type. In some embodiments, operation 306 is performed by a processor component the same as or similar to communications component 26 (shown in FIG. 1 and described herein).

At an operation 308, discharge date information from a facility of the first type associated with the patient is obtained. In some embodiments, operation 308 is performed by a processor component the same as or similar to communications component 26 (shown in FIG. 1 and described herein).

At an operation 310, a risk of readmission to a facility of the first type for the patient is determined based on the obtained patient demographics information, the disease information, the facility information, and the discharge date information. In some embodiments, operation 310 is performed by a processor component the same as or similar to risk determination component 28 (shown in FIG. 1 and described herein).

At an operation 312, a configuration of the patient interface computer system is caused to be modified based on the determined risk of readmission. In some embodiments, operation 312 is performed by a processor component the same as or similar to care plan component 30 (shown in FIG. 1 and described herein).

Although the description provided above provides detail for the purpose of illustration based on what is currently considered to be the most practical and preferred embodiments, it is to be understood that such detail is solely for that purpose and that the disclosure is not limited to the expressly disclosed embodiments, but, on the contrary, is intended to cover modifications and equivalent arrangements that are within the spirit and scope of the appended claims. For example, it is to be understood that the present disclosure contemplates that, to the extent possible, one or more features of any embodiment can be combined with one or more features of any other embodiment.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

What is claimed is:

1. A system configured to facilitate configuration modifications for a remote patient interface computer system based on risk of readmission of a patient, the system comprising:

a remote patient interface computer system comprising one or more sensors configured to provide real-time signals conveying information indicating a measurement of the patient, and a wearable device configured to (1) at least one of receive and send one or more program instructions and (2) at least one of spot-check, periodically monitor, and continuously monitor the patient;

a database of patient demographics information for a plurality of patients;

one or more processors configured by machine-readable instructions to: (i) obtain patient demographics information associated with a patient, the patient previously having been admitted at a facility of a first type; (ii) obtain disease information associated with the patient; (iii) obtain facility information associated with a facility of a second type to which the patient has been admitted subsequent to the facility of the first type, the facility information including one or more facility-specific factors associated with the facility of the second type; (iv) determine a risk of readmission to a facility of the first type for the patient based on the obtained patient demographics information, the disease information, and the facility information; and (v) cause a configuration of the remote patient interface computer system to be modified based on the determined risk of readmission; and a remote live audio-visual consultation system;

wherein causing a configuration of the remote patient interface computer system to be modified includes remotely changing an amount of monitoring of the patient with the one or more sensors, and wherein causing a configuration of the remote patient interface computer system to be modified further includes providing one or more of a notification, reminder, or direction(s) to the patient via the wearable device.

2. The system of claim 1, wherein the one or more facility-specific factors include one or more of the Centers for Medicare and Medicaid services rating, The Joint Commission certification status, a Resident Council meeting frequency, a Family Council meeting frequency, a number of deficiencies on a previous licensing and certification survey, visitation hour enforcement, a treating registered nurse to patient ratio, a licensed practical nurse and/or licensed vocational nurse to patient ratio, a geriatric nursing assistant and/or certified nursing assistant to patient ratio, information related to nurse use at the facility of the second type, a staff turnover rate, a root cause analysis percentage of unplanned admission and/or transfer to an emergency department, a return-to-hospital rate, or information related to a medical director of the facility of the second type.

3. The system of claim 1, wherein the one or more processors are configured to (i) assign a score to individual demographic-specific factors of the obtained patient demographics information, individual disease-specific factors of the disease information, and/or individual facility-specific factors of the facility information, and (ii) determine the risk of readmission to a facility of the first type based on the assigned scores.

4. The system of claim 1, wherein the one or more processors are further configured to notify one or more care givers regarding the patient's determined risk of readmission and/or a change in the determined risk of readmission.

5. A method for facilitating configuration modifications for a remote patient interface computer system based on risk of readmission of a patient with a system, the system comprising: (1) a remote patient interface computer system comprising one or more sensors configured to provide real-time signals conveying information indicating a measurement of the patient, and further comprising a wearable device, (2) one or more processors, and (3) a remote live audio-visual consultation system, the method comprising:

obtaining, with the one or more processors, patient demographics information associated with a patient from a database of the system comprising patient demographics information for a plurality of patients, the patient previously having been admitted at a facility of a first type;

obtaining, with the one or more processors, disease information associated with the patient;

obtaining, with the one or more processors, facility information associated with a facility of a second type to which the patient has been admitted subsequent to the facility of the first type, the facility information including one or more facility-specific factors associated with the facility of the second type;

determining, with the one or more processors, a risk of readmission to a facility of the first type for the patient based on the obtained patient demographics information, the disease information, and the facility information; and causing, with the one or more processors, a configuration of the remote patient interface computer system to be modified based on the determined risk of readmission;

wherein causing a configuration of the remote patient interface computer system to be modified includes remotely changing an amount of monitoring of the patient with the one or more sensors, and wherein the step of causing, with the one or more processors, a configuration of the remote patient interface computer system to be modified based on the determined risk of readmission comprises providing one or more of a notification, reminder, or direction(s) to the patient via the wearable device.

6. The method of claim 5, wherein the one or more facility-specific factors include one or more of the Centers for Medicare and Medicaid Services rating, The Joint Commission certification status, a Resident Council meeting frequency, a Family Council meeting frequency, a number of deficiencies on a previous licensing and certification survey, visitation hour enforcement, a treating registered nurse to patient ratio, a licensed practical nurse and/or licensed vocational nurse to patient ratio, a geriatric nursing assistant and/or certified nursing assistant to patient ratio, information related to nurse use at the facility of the second type, a staff turnover rate, a root cause analysis percentage of unplanned admission and/or transfer to an emergency department, a return-to-hospital rate, or information related to a medical director of the facility of the second type.

7. The method of claim 5, further comprising (i) assigning, with the one or more processors, a score to individual demographic-specific factors of the obtained patient demographics information, individual disease-specific factors of the disease information, and/or individual facility-specific factors of the facility information, and (ii) determining, with the one or more processors, the risk of readmission to a facility of the first type based on the assigned scores.

8. The method of claim 5, further comprising notifying one or more care givers regarding the patient's determined risk of readmission and/or a change in the determined risk of readmission.

9. The system of claim 1, wherein causing a configuration of the patient interface computer system to be modified further includes increasing or reducing user interface options associated with the wearable device.

10. The method of claim 5, wherein the step of causing, with the one or more processors, a configuration of the patient interface computer system to be modified based on the determined risk of readmission comprises increasing or reducing user interface options associated with the wearable device.

* * * * *